US00PP21467P2

(12) United States Plant Patent
Kordes

(10) Patent No.: US PP21,467 P2
(45) Date of Patent: Nov. 16, 2010

(54) SHRUB ROSE PLANT NAMED 'KORGELEFLO'

(50) Latin Name: *Rosa hybrida*
Varietal Denomination: KORgeleflo

(75) Inventor: Tim-Hermann Kordes, Klein Offenseth-Sparrieshoop (DE)

(73) Assignee: W. Kordes' Söhne Rosenachulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/583,068

(22) Filed: Aug. 12, 2009

(51) Int. Cl.
*A01H 5/00* (2006.01)

(52) U.S. Cl. ..... Plt./104
(58) Field of Classification Search ..... Plt./104
See application file for complete search history.

(56) References Cited

OTHER PUBLICATIONS

2008/1245, European Union CVPO summary, Aug. 15, 2008, European Union.

*Primary Examiner*—Susan B McCormick Ewoldt

(57) ABSTRACT

A new and distinct variety of rose with long lasting, yellow flowers, and attractive foliage with good disease resistance. It exhibits spreading growth with abundant flowers. The new variety propagates well from cuttings and by grafting. This new and distinct variety has shown to be uniform and stable in the resulting generations from asexual propagation.

1 Drawing Sheet

Genus, species and variety denomination: The botanical classification of the new rose plant is *Rosa hybrida*, 'KORgeleflo'.

BACKGROUND OF THE INVENTION

The new variety of rose plant of the present invention originated from a controlled crossing made in a rose breeding program between 'KORgosumu', a non-patented rose by the same breeder, and an 'un-named seedling'.

The controlled crossing was made during the summer of 2000. The following winter, Tim-Hermann Kordes planted the resulting seeds from the aforementioned hybridization in a glasshouse where they subsequently germinated and grew. Evaluations and observations were made on the resulting seedlings in a controlled environment in Offenseth-Sparrieshoop, Germany. The resulting seedlings exhibited distinctive physical and biological characteristics. The new rose plant 'KORgeleflo' was selected in May, 2001 from the seedling beds to be asexually propagated for further evaluation. The first asexual reproduction of 'KORgeleflo' was done by budding to seedling understocks in August, 2001 at the inventor's nursery in Offenseth-Sparrieshoop, Germany.

These initial and other subsequent propagations conducted in controlled environments demonstrate that 'KORgeleflo' reproduces true to type in successive generations of asexual reproduction.

SUMMARY OF THE INVENTION

The new rose plant may be distinguished from its seed parent, 'KORgosumu' by the following combination of characteristics:

1. The growth habit of the seed parent is bushy and upright, while the growth habit of 'KORgeleflo' is spreading.
2. The petal count of the seed parent is semi-double, while the petal count of 'KORgeleflo' is very double.

The new rose plant may be distinguished from its pollen parent, an 'un-named seedling' by the following combination of characteristics:

1. The flower color of the pollen parent is apricot, while the flower color of 'KORgeleflo' is yellow.
2. The growth habit of the pollen parent is upright, while the growth habit of 'KORgeleflo' is spreading.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORgeleflo' from all other varieties of which we are aware.

BRIEF DESCRIPTION OF THE DRAWING

The accompanying drawing shows as true as is reasonably possible to obtain in color photographs of this type, the typical characteristics of the buds, flowers, reproductive organs, leaves, hips, and stems of 'KORgeleflo'.

DETAILED BOTANICAL DESCRIPTION

The following is a description of 'KORgeleflo', as observed growing in October, 2008 in a nursery in Jackson County, Oreg. on plants of three years of age. Color references are made using The Royal Horticultural Society (London, England) Colour Chart, 2001 except where common terms of color are used.

For a comparison, several physical characteristics of the rose variety 'KORsupigel', a rose variety from the same inventor described and illustrated in U.S. Plant Pat. No. 19,601 and filed on Dec. 30, 2008 are compared to 'KORgeleflo' in Chart 1.

CHART 1

| Characteristic | 'KORgeleflo' | 'KORsupigel' |
|---|---|---|
| Overall height | 60-65 cm | 40-50 cm |
| Petal count | 40-45 | 40-60 |
| Average leaf size | 40 mm (1) × 25 mm (w) | 75 mm (1) × 50 mm (w) |

Parents:

*Seed parent.*—'KORgosumu'.

*Pollen parent.*—'un-named seedling'.

Classification:

*Botanical classification.*—*Rosa hybrida*, 'KORgeleflo'.

*Commercial classification.*—Shrub.

FLOWER AND FLOWER BUD

Blooming habit: Continuous.

Flower bud:

*Size.*—Upon opening, 25-27 mm in length from base of receptacle to end of bud and 22-24 mm diameter at its widest point.

*Bud form.*—Long. Pointed ovoid.

*Bud color.*—As sepals first unfold, bud color is Green-Yellow Group 1C. When ¼ open, the upper surface of petals is Yellow Group 5B and Yellow Group 5C and the lower surface is Yellow Group 5C. Guard petals are Yellow Green Group 145A, 145B, and 145C.

*Sepals.*—Size: Average 20-25 mm long×9-10 mm wide. Shape: Sepals generally subulate. Sepal apex is generally cirrose. Weak foliaceous appendages on three of the five sepals. Base is flat at union with receptacle. Quantity: Five. Margins: With stipitate glands. Surface texture: Inner side: Covered in fine white hairs. Outer surface: Smooth. Stipitate glands are absent. Color: Upper surface Yellow-Green Group 144A and Yellow-Green Group 144B. Lower surface Yellow-Green Group 144A. Intonations of Greyed-Red Group 182A.

Receptacle:

*Surface.*—Smooth.

*Color.*—Yellow-Green Group 144A.

*Shape.*—Funnel shaped.

*Size.*—7-8 mm (h)×6-7 mm (w).

Peduncle:

*Surface.*—With stipitate glands.

*Length.*—30-35 mm average length.

*Diameter.*—2.0-2.5 mm average diameter.

*Color.*—Yellow-Green Group 144A.

*Strength.*—Moderate.

*Borne.*—Multiple buds per stem. Generally, 3-5 buds per flowering stem.

*Anthocyanin.*—Greyed-Red Group 178A.

Flower bloom:

*Fragrance.*—Strong sweet fragrance.

*Duration.*—On the plant 5-6 days. Long lasting. Senesced petals drop away cleanly.

*Size.*—Medium flowered garden rose. When open, the average flower diameter is 65-75 mm and the average flower height is 35-40 mm.

*Form.*—Shape of flower when viewed from the side: Upon opening, upper part: Flattened convex. Upon opening, lower part: Flat. Open flower, upper part: Flattened convex. Open flower, lower part: Concave.

Color:

*Upon opening, petals.*—Outermost petals: Outer side: Yellow Group 4C and Yellow Group 4D. Inner side: Yellow Group 5B and Yellow Group 5C. Innermost petals: Outer side: Yellow Group 4C. Inner side: Yellow Group 4C.

*Upon opening, basal petal spots.*—Basal petal spot, outermost petals: Outer side: Green-Yellow Group 1B. Inner side: Yellow Group 5A. Basal petal spot, innermost petals: Outer side: Yellow Group 5A. Inner side: Yellow Group 5A.

*After opening, petals.*—Outermost petals: Outer side: Yellow Group 4D. Inner side: Yellow Group 4D. Innermost petals: Outer side: Yellow Group 5D. Inner side: Yellow Group 5D.

*After opening, basal petal spots.*—Basal petal spot, outermost petals: Outer side: Yellow Group 4B. Inner side: Yellow Group 4B. Basal petal spot, innermost petals: Outer side: Yellow Group 5B. Inner side: Yellow Group 5B.

General tonality: On open flower Yellow Group 4C. No change in the general tonality at the end of the 7$^{th}$ day. Afterwards, general tonality is Yellow Group 4D .

Petals:

*Petal count.*—Approximately 40-45 petals under normal conditions.

*Petal reflex.*—Petals reflex somewhat.

*Petal edge.*—Entire with slight undulations in center of margin.

*Petal shape.*—Deltoid. Apex shape is round. Shape of base is acute.

*Petal size.*—30-35 mm long; 25-30 mm wide.

*Thickness.*—Average.

*Petal arrangement.*—Generally in a regular pattern with overlapping edges.

Petaloids: Present.

*Petaloid count.*—Average of 5-10 per flower.

*Petaloid edge.*—Undulated.

*Petaloid texture.*—Undulated.

*Petaloid shape.*—Linear to elliptic. Shape of base is pointed. Shape of apex is round and ruffled.

*Petaloid size.*—Petaloids are 15 mm long and 7 mm wide.

*Petaloid color.*—Color of inner side is Yellow Group 6A. Color of outer side is Yellow Group 6A.

Reproductive organs:

*Pistils.*—Approximately 20-30 present. Stigmas: Location: Slightly inferior in position to anthers. Color: Green-Yellow Group 1C. Styles: Length: 5-6 mm long. Color: Green-Yellow Group 1C.

*Stamens.*—Approximately 45-50 on average and regularly arranged. Anthers: Size: 2-2.5 mm long. Color: Yellow-Orange Group 22A. Pollen: Absent. Filaments: Color: Yellow Group 2A. Length: 6-7 mm.

THE PLANT

*Plant growth.*—Vigorous, spreading habit. When grown as a budded nursery plant the average plant height is 60-65 cm and the average plant width is 50-55 cm.

*Stems.*—Stem color: Young wood: Yellow-Green Group 144A. Older Wood: Yellow-Green Group 146B. Stem surface: Young wood: Smooth. Older wood: Rough.

*Prickles.*—Present. Incidence: 7-12 per 10 cm of stem. Size: Average length: 6-7 mm. Color: Immature prickles: Greyed-Yellow Group 160B with Anthocyanin of Greyed-Red Group 181B. Mature prickles: Greyed-Orange Group 166A and 166B. Senescing to Greyed-Orange Group N167B. Shape: Deeply concave. Anthocyanin: Color: Greyed-Red Group 181B.

*Leaves and leaflets.*—Normally 5-7 leaflets on normal leaves in middle of the stem. Leaf size: 100 mm (1)× 65 mm (w). Quantity: Abundant. Texture: Upper side of leaflet: Glossy. Smooth. Under side of leaflet: Matte. Rough. Thin. Color, mature foliage: Upper Leaf Surface: Green Group 137A. Lower Leaf Surface: Yellow-Green Group 147B. Color, juvenile foliage: Upper Leaf Surface: Green Group 137A. Lower Leaf Surface: Yellow-Green Group 147B. Anthocyanin intonation: Absent.

*Stipules.*—Size: 15 mm long. 7 mm between the tips of the stipule. Main body of stipule 5 mm in width. Shape: Longitudinally flanged or winged along middle. Stipule color: Green Group 138A. Anthocyanin: Greyed-Purple Group 184B. Presence of stipitate glands: Present on margins. Margins: With stipitate glands.

*Petiole.*—Length: 8-11 mm. Diameter: 1.0 mm. Petiole color: Green Group 138A. Anthocyanin present on juvenile tissue, Greyed-Purple Group 184B. Underneath: Occasional prickle. Stipitate glands: Present on margins.

*Petiole rachis.*—Length: 18-22 mm. Diameter: 1.0 mm. Color: Green Group 138A. Anthocyanin present on juvenile tissue, Greyed-Purple Group 184B. Margins: Very few stipitate glands present. Prickles: Occasional. Stipitate glands: Few stipitate glands on margins.

*Leaflets.*—Size: Average size of the terminal leaflet is 40 mm (1)×25 mm (w). Shape: Ovate. Base: Ovate. Apex: Acute. Margins: Serrated. Texture: Thin and leathery.

Hips/seed formation: Color: Yellow-Green Group 144B. Size: 10 mm (1)×10 mm (w).

Winter hardiness: To date, the variety has been grown successfully in Zone 5.

Disease resistance: Above average resistance to Powdery mildew (*Sphaerotheca pannosa*), rust (*P. disciflorum*), blackspot (*Diplocarpon rosae*), and Botrytis (*Botrytis cinerea*) diseases under normal growing conditions.

I claim:

1. A new and distinct variety of rose plant as herein illustrated and described:

(a) Forms attractive, long lasting yellow flowers;
(b) Exhibits spreading growth habit;
(c) Propagates well using traditional methods, and;
(d) Exhibits very good resistance to disease under normal growing conditions, substantially as herein illustrated and described.

* * * * *

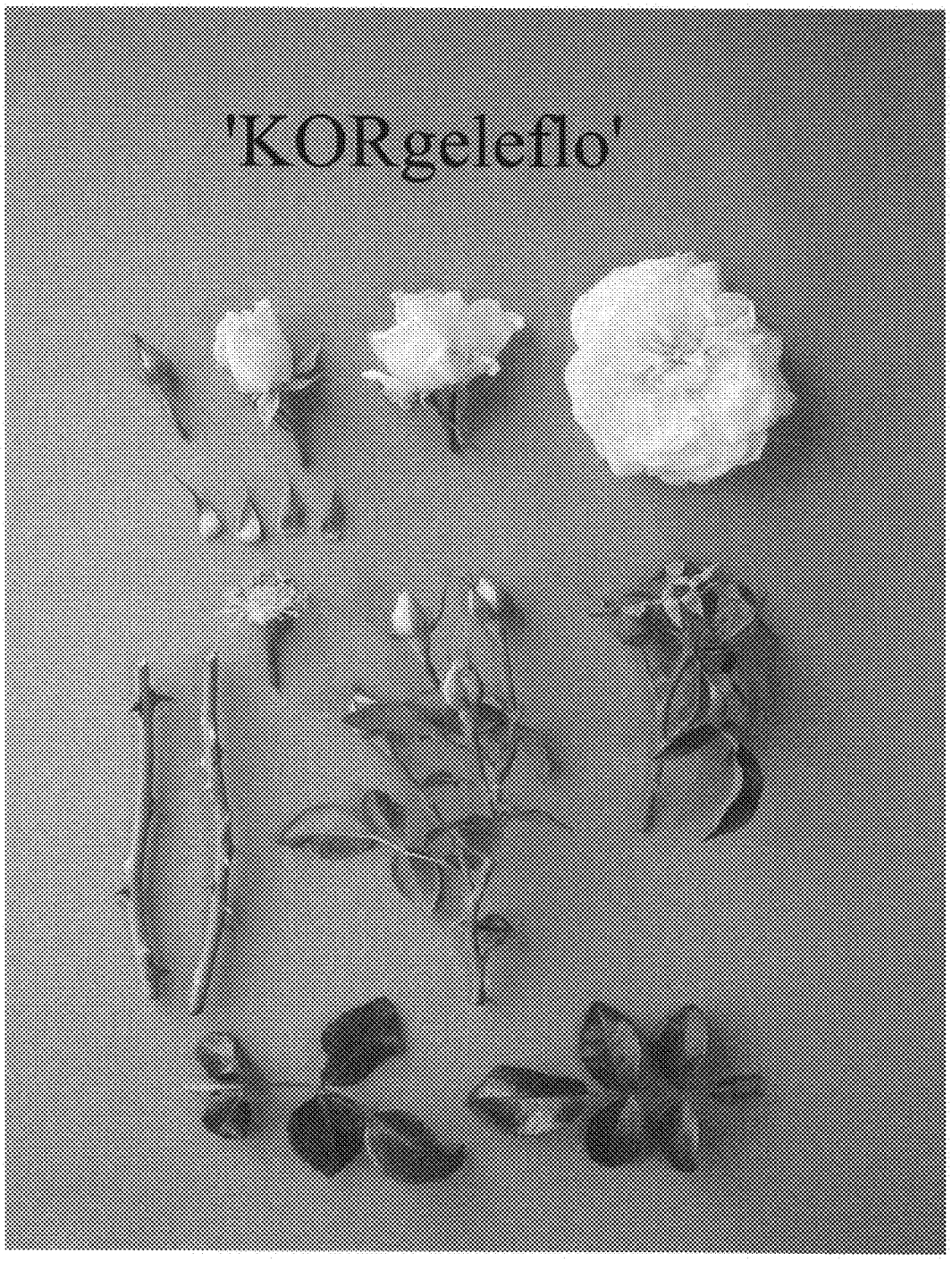
'KORgeleflo'